United States Patent
Riether et al.

(10) Patent No.: US 9,810,706 B2
(45) Date of Patent: Nov. 7, 2017

(54) VERTICAL CONVEYING DEVICE, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Christian Riether, Muehltal (DE); Hans Schneider, Schwaikheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/665,415

(22) Filed: Mar. 23, 2015

(65) Prior Publication Data

US 2015/0276778 A1    Oct. 1, 2015

(30) Foreign Application Priority Data

Mar. 31, 2014    (EP) .................................... 14162940

(51) Int. Cl.
| | |
|---|---|
| *G01N 35/04* | (2006.01) |
| *G01N 35/10* | (2006.01) |
| *B66B 11/04* | (2006.01) |
| *B65G 15/58* | (2006.01) |

(52) U.S. Cl.
CPC .............. *G01N 35/10* (2013.01); *B66B 11/04* (2013.01); *G01N 35/04* (2013.01); *B65G 15/58* (2013.01); *G01N 2035/0477* (2013.01); *G01N 2035/0484* (2013.01)

(58) Field of Classification Search
CPC ... G01N 2035/0477; G01N 2035/0484; B65G 15/58
See application file for complete search history.

(56) References Cited

U.S. PATENT DOCUMENTS

| | | | |
|---|---|---|---|
| 3,273,727 A | 9/1966 | Rogers et al. | |
| 2,653,485 A | 4/1972 | Donlon | |
| 3,653,485 A | 4/1972 | Donlon | |
| 3,901,656 A | 8/1975 | Durkos et al. | |
| 4,150,666 A | 4/1979 | Brush | |
| 4,395,164 A | 7/1983 | Beltrop | |
| 4,544,068 A | 10/1985 | Cohen | |
| 4,771,237 A | 9/1988 | Daley | |
| 5,120,506 A | 6/1992 | Saito et al. | |
| 5,295,570 A * | 3/1994 | Grecksch | B65G 21/2009 198/465.1 |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — P. Kathryn Wright
(74) *Attorney, Agent, or Firm* — Roche Diagnostics Operations, Inc.

(57) ABSTRACT

A vertical conveying device for the transport of sample container carriers having sample tubes received therein between a bottom level and a top level of a sample distribution system is presented. The vertical conveying device comprises a plurality of conveying surfaces which are movable along a circulating path. A sample distribution system having such a vertical conveying device and to a laboratory automation system having such a sample distribution system are also presented.

8 Claims, 1 Drawing Sheet

(56) References Cited

U.S. PATENT DOCUMENTS

| | | |
|---|---|---|
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A * | 6/1997 | Mori ............... H01L 21/67167 104/284 |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,850,914 B2 | 12/2010 | Veiner et al. |
| 7,858,033 B2 | 12/2010 | Itoh |
| 7,875,254 B2 | 1/2011 | Garton |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug |
| 2012/0037696 A1 | 2/2012 | Lavi |
| 2012/0129673 A1 | 5/2012 | Fukugaki et al. |
| 2012/0178170 A1 | 7/2012 | Van Pract |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether et al. |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |

(56) References Cited

FOREIGN PATENT DOCUMENTS

| | | |
|---|---|---|
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1966 |
| JP | S56-147209 A | 11/1981 |
| JP | 60-223481 A | 11/1985 |
| JP | 61-081323 A | 4/1986 |
| JP | S61-069604 | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-026808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/085670 A1 | 7/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

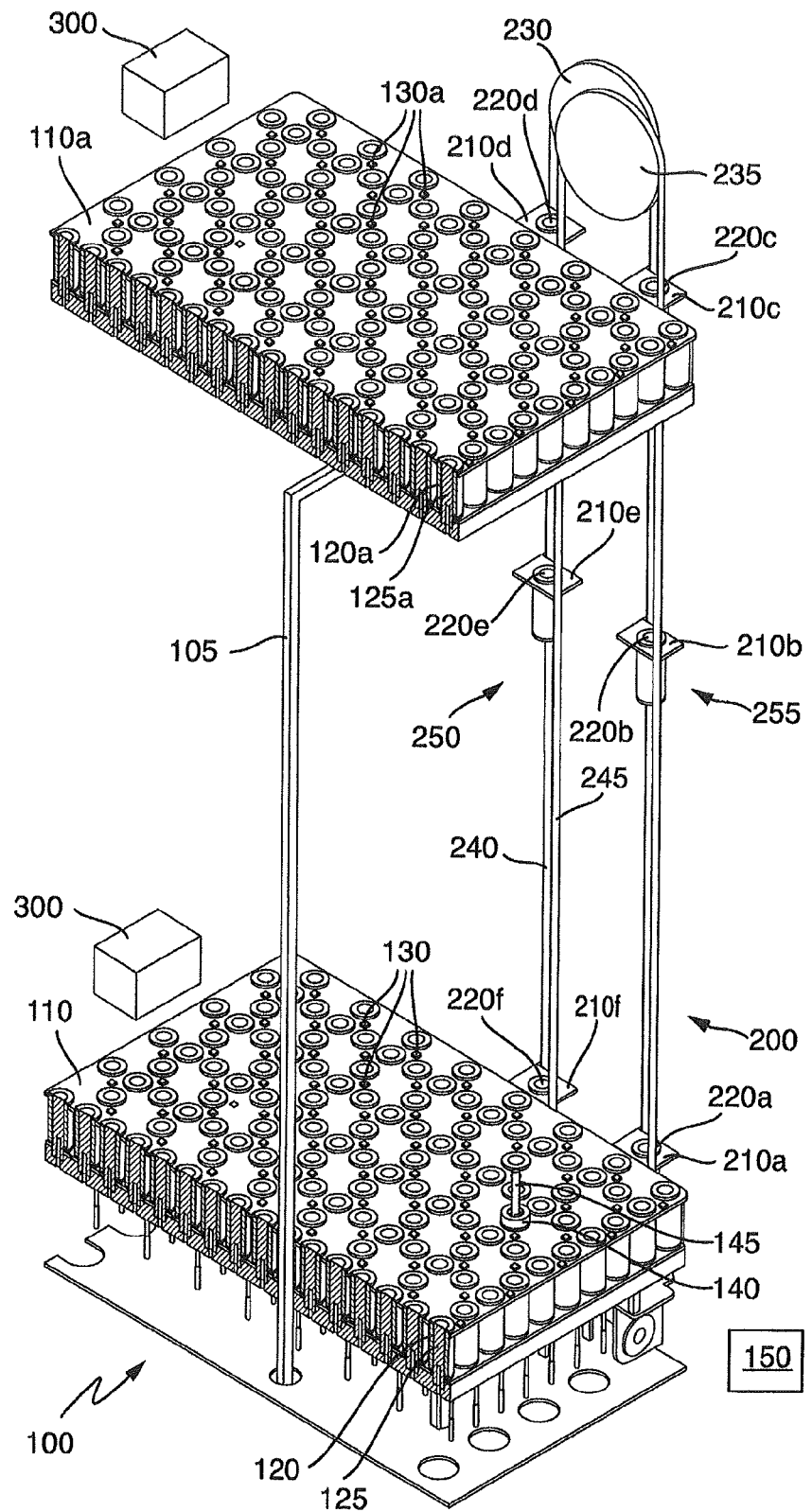

VERTICAL CONVEYING DEVICE, LABORATORY SAMPLE DISTRIBUTION SYSTEM AND LABORATORY AUTOMATION SYSTEM

CROSS-REFERENCE TO RELATED APPLICATIONS

This application claims priority to EP 14162940.2, filed Mar. 31, 2014, which is hereby incorporated by reference.

BACKGROUND

The present disclosure generally relates to a vertical conveying device for the transport of sample containers, which are received in respective sample container carriers, to a sample distribution system having such a vertical conveying device and to a laboratory automation system having such a sample distribution system.

Sample containers are typically elongated vessels, which are open at the one end, produced in the majority of cases from transparent glass or plastics material and are used for preserving and for transporting in the majority of cases liquid samples. These types of samples are, for example, blood samples. Sample distribution systems are used, for example, in laboratory automation systems in order to transport samples in sample containers to a plurality of different stations of the laboratory automation system.

Therefore, this is a need for to provide a vertical conveying device by way of which sample container carriers can be transported between different levels of a sample distribution system, to provide a sample distribution system having such a vertical conveying device, and to provide a laboratory automation system having such a sample distribution system.

SUMMARY

According to the present disclosure, a vertical conveying device to transport sample containers contained in sample container carriers between a bottom level and a top level of a sample distribution system is presented. Each sample container carrier can comprise at least one magnetically active element to interact with a magnetic field generated by at least one electromagnetic actuator such that a driving force is applied to the sample container carrier. The vertical conveying device can comprise a plurality of conveying elements having conveying surfaces for receiving at least one sample container carrier; a circulating device to circulate the conveying elements between the bottom level and the top level in operation such that the conveying surfaces continuously remain aligned horizontally during the circulation; and at least one electromagnetic actuator to apply a driving force to a sample container carrier to be driven on one of the conveying surfaces.

Accordingly, it is a feature of the embodiments of the present disclosure to provide a vertical conveying device by way of which sample container carriers can be transported between different levels of a sample distribution system, to provide a sample distribution system having such a vertical conveying device, and to provide a laboratory automation system having such a sample distribution system. Other features of the embodiments of the present disclosure will be apparent in light of the description of the disclosure embodied herein.

BRIEF DESCRIPTION OF THE SEVERAL VIEWS OF THE DRAWING

The following detailed description of specific embodiments of the present disclosure can be best understood when read in conjunction with the following drawing, where like structure is indicated with like reference numerals and in which:

FIG. 1 illustrates a sample distribution system comprising a vertical conveying device according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A vertical conveying device for the transport of sample containers which are received in sample container carriers between a bottom level and a top level of a sample distribution system is presented. Sample container carriers, which are not a component part of the vertical conveying device, can comprise at least one magnetically active element which can be realized for the purpose of interacting in such a manner with a magnetic field generated by at least one electromagnetic actuator that a driving force is applied to the sample container carrier.

The vertical conveying device can comprise a plurality of conveying elements each of which can comprise a conveying surface which is provided for receiving or for placing on and carrying at least one sample container carrier, a circulating device which is realized for the purpose of rotatingly moving or circulating the conveying elements in operation between the bottom level and the top level, wherein the respective conveying surfaces can be or can remain continuously horizontally aligned during the rotating movement, and at least one electromagnetic actuator which can also be designated as a conveyor surface actuator and can be realized for the purpose of applying a driving force on a sample container carrier, which can be situated on one of the conveying surfaces.

The vertical conveying device can enable sample container carriers with sample containers received therein to be transported between different levels of a sample distribution system which can take up little space. Transport may be affected vertically with or without a horizontal component. This can enable the vertical conveying device and a sample distribution system which can include the device to be designed in a particularly compact manner.

Sample container carriers can typically (not necessarily) be realized in a round manner and can be provided with a magnetically active element in the form of a permanent magnet. They can comprise typically on their top surface a holding device, in order to receive a sample tube, which can be realized, for example, similarly to a test tube or can be realized as a test tube. Sample container carriers can be used, for example, for transporting the sample container between pre-analytical, analytical and/or post-analytical stations of a laboratory automation system. A pre-analytical station can usually serve for preparing samples or sample containers. An analytical station can be realized, for example, for the purpose of using a sample or part of the sample and a reagent in order to generate a measurable signal, on the basis of which it can be possible to determine whether and where applicable in which concentration the analyte is present. A post-analytical station can usually serve for post-processing samples or sample containers.

The conveying elements of the vertical conveying device, as a result of their continuously horizontal alignment, can make it possible for a sample container carrier to be able to be moved onto the conveying surface and to be transported without falling off or tipping over from the conveying surface. It can be understood that in principle it can also be possible to move several sample container carriers onto one single conveying surface. The conveying elements with their respective conveying surfaces can be realized in the manner of a paternoster or an escalator.

According to one embodiment, the electromagnetic (conveying surface) actuator, e.g. in the form of an electromagnet, can be realized in such a manner that it can circulate together with the associated conveying surface under which it can be arranged. An associated electromagnetic (conveying surface) actuator can typically be arranged under each conveying surface. Alternatively, a single stationary electromagnetic (conveying surface) actuator may be used, which can be moved under a conveying surface when the conveying surface is loaded and/or is to be unloaded. It can be understood that other mechanisms can also be used in place of electromagnetic (conveying surface) actuators for moving sample container carriers onto the transport surface. It can be possible to use a gripper, a drag band or another structure, for example. An electromagnetic (conveying surface) actuator can be, in particular, an electromagnet, in a coil-shaped electromagnet having a core.

By an electromagnetic (conveying surface) actuator, a sample container carrier can be moved onto the conveying surface, can be held on the conveying surface and/or removed from the conveying surface. This can enable simple handling of the sample container carrier, wherein complicated devices such as, for example, grippers or the like can be avoided.

The circulating device can move the conveying elements along a circulating path described by all the conveying elements. This can correspond in principle to the realization of a paternoster or an escalator. Consequently, almost continuous transport between different levels can be achieved.

The vertical conveying device can comprise a plurality of conveying elements which can be arranged spaced apart from one another at regular distances along the circulation path. Consequently, the handling of the vertical conveying device can be simplified. It can be assumed, for example, that a transport operation can be terminated after a defined operation of the vertical conveying device, for example for a certain period of time. In a corresponding manner, a conveying surface can once again be available for a transport operation. A distance between adjacent conveying elements can be dimensioned such that a sample container carrier having an accommodated container can be movable between two adjacent conveying surfaces. It can be advantageous that certain conveying surfaces are at a certain proportion to certain other conveying surfaces, such that sample container carriers may be loaded at the top and at the bottom at the same time.

The circulating path can comprise a first vertical portion and a second vertical portion which can be parallel thereto. The portions can extend between the bottom level and the top level. In operation, the circulating device can move the conveying elements along the first vertical portion from the bottom level to the top level and additionally can move the conveying elements along the second vertical portion from the top level to the bottom level.

The circulating device can comprise a first top wheel, a first bottom wheel and a first band. The first band can rotate in a semi-circular manner about the first top wheel and the first bottom wheel and can be tensioned between the first top wheel and the first bottom wheel. The first top wheel and/or the first bottom wheel can be driven when the circulating device is operating. The conveying elements can be fastened on the first band. The circulating device can comprise a second top wheel, a second bottom wheel and a second band. The second band can rotate in a semi-circular manner about the second top wheel and the second bottom wheel and can be tensioned between the second top wheel and the second bottom wheel. The second top wheel and/or the second bottom wheel, when the circulating device is operating, can be driven synchronously with the first top wheel or the first bottom wheel. The conveying elements can be fastened on the first band and on the second band.

A respective conveying element can comprise a detection device for a sample container carrier which can be situated on the conveying surface of the conveying element. Consequently, it can be detected when the vertical conveying device is operating whether a sample container carrier is situated on the respective conveying surface and consequently reliability in operation can be increased. Such a detecting device can be realized as a Hall sensor.

A sample distribution system can comprise a plurality of sample container carriers for receiving one or several sample containers. A respective sample container carrier can comprise at least one magnetically active element which can be realized for the purpose of interacting in such a manner with a magnetic field which can be generated by at least one electromagnetic actuator that a driving force applied to the sample container carrier. The sample distribution system can also comprise a bottom transport surface and a top transport surface. The top transport surface can be arranged vertically higher in relation to the bottom transport surface. The bottom and top transport surfaces can be realized for the purpose of carrying sample container carriers. The sample distribution system can also comprise a plurality of first electromagnetic actuators which can also be designated as transport surface actuators and can be arranged in a stationary manner under the bottom transport surface. The first plurality of electromagnetic (transport surface) actuators can be realized for the purpose of moving a sample container carrier, which can be arranged on the bottom transport surface, as a result of exerting a magnetic force onto the sample container carrier. The sample distribution system can also comprise a plurality of second electromagnetic actuators which can also be designated as transport surface actuators and which can be arranged in a stationary manner under the top transport surface. The second plurality of electromagnetic (transport surface) actuators can be realized for the purpose of moving a sample container carrier, which can be arranged on the top transport surface, as a result of exerting a magnetic force onto the sample container carrier. The sample distribution system can also comprise an above-described vertical conveying device. The bottom transport surface can correspond to the bottom level and the top transport surface can correspond to the top level. Finally, the sample distribution system can also comprise a control device which can be adapted to actuate the electromagnetic (transport surface) actuators which can be arranged under the transport surfaces in such a manner that a sample container carrier can be moved along an associated definable movement path on the transport surfaces, to actuate the at least one electromagnetic (conveying surface) actuator and/or the electromagnetic (transport surface) actuators which can be arranged under the transport surfaces in such a manner that a sample container carrier can be moved from the transport surface in the direction of one of the conveying surfaces or from one of the conveying surfaces in the direction of one of the transport surfaces and to control the circulating device in such a manner that the sample container carriers can be transported between the bottom level and the top level.

The sample container carriers can be realized in a round manner which can avoid having to observe a preferred orientation. A magnetically active element in a sample container carrier can be a permanent magnet or another magnetic material.

The top transport surface can be arranged higher in the vertical direction than the bottom transport surface. This can serve, for example, for the purpose of coupling analysis instruments or other devices operatively with the sample distribution system, the inlet and/or outlet of which can be situated at different heights. In addition, it can be possible to use different levels in order to realize different transport tasks. For example, a bottom level can be used for the transport of sample container carriers over longer sections, whereas a top level can be used for moving the sample container carriers to analysis instruments or other stations. It can be understood that the reverse case can also be possible, for example.

The electromagnetic actuators can be electromagnets, for example in the form of coils. The coils can comprise a ferromagnetic core which can strengthen the magnetic action. As a result of interaction between a magnetic field generated by the electromagnetic actuators and the magnetically active element in the sample container carrier, a sample container carrier can be moved over the transport surface. The electromagnetic actuators can be actuated in a suitable manner for this purpose. The electromagnetic actuators can be distributed in the manner of a matrix such that a two-dimensional movement over the transport surface is possible.

By use of the vertical conveying device, sample container carriers with sample containers received therein can be transported between the bottom level and the top level. It can be understood that a sample distribution system can also comprise more than two levels, for example three or four levels. This can mean the flexibility can be further increased. The vertical conveying device can easily be adaptable to such types of realizations.

The control device can be realized, for example, as a computer, a microcomputer, a microprocessor, programmable logic controller (PLC), a user-specific integrated circuit (ASIC) or in another manner. For example, it can comprise a processor and storage, code being stored in the storage, in the case of the execution of which the processor can behave in a defined manner. A sample container carrier which is moved from the transport surface in the direction of the conveying surface can typically be a sample container carrier to be conveyed. It can be moved therefore to another level by the vertical conveying device. A sample container carrier which is moved in the designated manner from the conveying surface in the direction of the transport surface can typically be a conveyed sample container carrier which has been transported by the vertical conveying device from another level to the current level and can then to be moved to the transport surface of the corresponding level.

The control device can be realized for the purpose of transporting a sample container carrier from the bottom transport surface to the top transport surface by operating the circulating device of the vertical conveying device up until one of the conveying elements is situated in a position in which the conveying surface of the conveying element forms a level extension of the bottom transport surface, moving the sample container carrier to the conveying element by the first electromagnetic (transport surface) actuators, moving the sample container carrier onto the conveying surface of the conveying element by the electromagnetic (conveyor surface) actuator or actuators, operating the circulating device of the vertical conveying device up until the conveying element is situated in a position in which the conveying surface forms a level extension of the top transport surface and moving the sample container carrier from the conveying surface onto the top transport surface by the electromagnetic (conveyor surface) actuator or actuators.

The control device can be realized for the purpose of bringing about a transport of a sample container carrier from the top transport surface to the bottom transport surface by driving the circulating device of the vertical conveying device up until one of the conveying elements is situated in a position in which the conveying surface of the conveying element forms a level extension of the top transport surface, moving the sample container carrier to the conveying element by the second electromagnetic (transport surface) actuators, moving the sample container carrier onto the conveying surface of the conveying element the electromagnetic (conveyor surface) actuator or actuators, driving the circulating device of the vertical conveying device up until the conveying element is situated in a position in which the conveying surface of the conveying element forms a level extension of the bottom transport surface and moving the sample container carrier from the conveying surface onto the bottom transport surface by the electromagnetic (conveyor surface) actuator or actuators.

The described realizations of the control device can enable sample container carriers to be transported between the top and the bottom level. The control device can be realized for the purpose of being able to move both a sample container carrier from the bottom transport surface onto the top transport surface and also a sample container carrier from the top transport surface onto the bottom transport surface in the manner just described.

The control device can be realized for the purpose of moving the sample container carrier onto the top or bottom transport surface also by the electromagnetic (conveyor surface) actuator. This can be in particular when a sample container carrier has been transported to the corresponding transport surface and is then to be moved onto the transport surface. A repelling force, for example, can be exerted onto the sample container carrier in this way.

The bottom transport surface and the top transport surface can be divided into logic fields, each logic field being associated in each case with an electromagnetic actuator from the number of first or second electromagnetic actuators. In addition, each conveying surface of the vertical conveying device can form a further logic field. The control device can handle a respective logic field, which is formed by a conveying surface, as a logic field of one of the transport surfaces when the conveying surface forms a level extension of the respective transport surface. This can enable particularly simple actuation of the electromagnetic actuators by the control device. When a conveying surface forms a level extension of the respective transport surface, there no longer needs to be differentiation between logic fields of the transport surface and of the conveying surface.

The vertical conveying device can be realized as an optional module of a unit which can support the top transport surface and the bottom transport surface. This can enable a simple and reliable realization.

The control device can be realized for the purpose of bringing about bidirectional transport of the sample container carriers between the transport surfaces by means of the vertical conveying device.

The laboratory automation system can comprise a plurality (for example, between two and twenty) of pre-analytical and/or analytical and/or post-analytical stations which can be realized for the purpose of processing or handling sample containers and/or samples contained in the sample containers. The processing or handling can include, for example, reading a barcode, removing a cap from the tube, centrifuging the sample, aliquoting the sample, analyzing the sample etc. The laboratory automation system can additionally comprise a sample distribution system for transporting the sample containers between the pre-analytical, analytical and post-analytical stations.

The pre-analytical, analytical and post-analytical stations can comprise, for example, at least one station from the list of following stations: a cap-removing station for removing caps or closures on sample tubes, a cap-positing station for placing caps or closures in position on sample tubes, an aliquoting station for aliquoting samples, a centrifugal station for centrifuging samples, an archiving station for archiving samples, a pipetting station for pipetting, a sorting station for sorting samples or sample tubes, a sample tube type-determining station for determining a type of sample tube and a sample quality-determining station for determining a sample quality.

FIG. 1 shows a sample distribution system 100. It can comprise a bottom transport surface 110 and a top transport surface 110a. The bottom transport surface 110 can correspond to a bottom level of the sample distribution system 100. The top transport surface 110a can correspond to a top level of the sample distribution system 100.

A plurality of first electromagnetic (transport surface) actuators in the form of coils 120 with respective cores 125 can be arranged below the bottom transport surface 110. In a corresponding manner, a plurality of second electromagnetic (transport surface) actuators in the form of coils 120a with respective cores 125a can be arranged below the top transport surface 110a. A sample container carrier 140 with a sample container received therein in the form of a sample tube 145 can be situated on the bottom transport surface 110. The sample container carrier 140 can comprise a magnetically active element in the form of a permanent magnet such that a force can be exerted onto the sample container carrier 140 as a result of actuating the electromagnets 120, 120a in a suitable manner and consequently the sample container carrier can be moved over the bottom transport surface 110 or the top transport surface 110a.

The top transport surface 110a can be held above the bottom transport surface 110 by a plurality of supports 105, wherein in the present case, only one single support 105 is shown as an example.

The sample distribution system 100 can further comprise a vertical conveying device 200 which can serve for the purpose of transporting sample container carriers 140 with sample tubes 145 received therein in a bidirectional manner between the bottom transport surface 110 and the top transport surface 110a.

The sample distribution system 100 can further comprise a control device 150 which can be realized for the purpose of controlling the electromagnets 120, 120a and the vertical conveying device 200. To this end, the control device 150 can be capable of moving a sample container carrier 140 over the bottom transport surface 110 or the top transport surface 110a as a result of actuating the electromagnetic actuators 120, 120a in a suitable manner.

The vertical conveying device 200 can comprise a total of six conveying surfaces 210a, 210b, 210c, 210d, 210e, 210f. An electromagnetic (conveyor surface) actuator in the form of an electromagnet 220a, 220b, 220c, 220d, 220e, 220f can be arranged below a conveying surface 210a, 210b, 210c, 210d, 210e, 210f. By use of the electromagnets 220a, 220b, 220c, 220d, 220e, 220f, the sample container carrier 140 can be moved or pulled onto the conveying surface 210a, 210b, 210c, 210d, 210e, 210f, held on the conveying surface and moved or pushed from the conveying surface onto one of the transport surfaces 110, 110a. The electromagnets 220a, 220b, 220c, 220d, 220e, 220f can also be actuatable by the control device 150. In addition, it can be detected as a result of an induction measurement by the electromagnets 220a, 220b, 220c, 220d, 220e, 220f whether a sample container carrier 140 can be situated on the conveying surface 210a, 210b, 210c, 210d, 210e, 210f.

A respective conveying surface 210a, 210b, 210c, 210d, 210e, 210f and a respective electromagnet 220a, 220b, 220c, 220d, 220e, 220f together form a conveying element. The conveying surfaces 210a, 210b, 210c, 210d, 210e, 210f can be arranged along a first band 240 and a second band 245. The two bands 240, 245, in this case, can define the position of the conveying surface 210a, 210b, 210c, 210d, 210e, 210f and ensure that a conveying surface 210a, 210b, 210c, 210d, 210e, 210f can and can remain aligned horizontally. The first band 240 can extend around a first top wheel 230. The second band 245 can extend around a second top wheel 235. The bands 240, 245 can also extend about corresponding first and second bottom wheels which, however, cannot be seen in FIG. 1. The bands 240, 245 together with the wheels 230, 235 can form a circulating device in form of a paternoster.

The conveying surfaces 210a, 210b, 210c, 210d, 210e, 210f can be arranged at regular distances along the bands 240, 245. By use of the top wheels 230, 235, which can both be drivable, the conveying surfaces 210a, 210b, 210c, 210d, 210e, 210f can circulate, i.e. to be rotatingly moved. The drive of the top wheels 230, 235 can be controllable by the control device 150 such that the control device 150 can use the vertical conveying device 200 to transport sample container carriers 140 with sample tubes 145 received therein between the bottom transport surface 110 and the top transport surface 110a.

In the state shown in FIG. 1, the transport surfaces 210a, 210c, 210d, and 210f can be arranged such that they form a level extension of the bottom transport surface 110 or the top transport surface 110a. The state can be used for the purpose of moving a sample container carrier 140 onto the respective transport surface 210a, 210c, 210d, 210f. The transport device 200 can then be put into motion such that the sample container carrier 140 can be transported to the other one of the two transport surfaces 110, 110a. There it can be moved by the electromagnets 120, 120a, 220a, 220b, 220c, 220d, 220e, 220f onto the respective transport surface 110, 110a.

The transport between the transport surfaces 110, 110a, in this case, can run along a first vertical portion 250 from the bottom transport surface 110 to the top transport surface 110a. It can run furthermore along a second vertical portion 255 which can be parallel thereto from the top transport surface 110a to the bottom transport surface 110.

The described realization of a vertical conveying device 200 can enable simple, reliable and space-saving bidirectional transport of sample container carriers 140 with sample tubes 145 received therein between the bottom transport surface 110 and the top transport surface 110a. As a result of the almost continuous operation of the vertical conveying device 200, a high throughput can be possible.

The sample distribution system 100 can be a component part of a laboratory automation system comprising a plurality of pre-analytical, analytical and post-analytical stations 300 which can be arranged adjoining the transport surfaces 110 and/or 110a. The sample distribution system 100 can serve for transporting the sample containers between the stations.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A sample distribution system, the sample distribution system comprising:
    a plurality of sample container carders for receiving one or more sample containers, wherein a sample container carrier comprises at least one magnetically active element to interact with a magnetic field generated by at least one electromagnetic actuator such that a driving force is applied to the sample container carrier;
    a bottom transport surface and a top transport surface arranged vertically higher in relation to the bottom transport surface, the bottom transport surface and the top transport surface carry the sample container carriers;
    a plurality of first electromagnetic actuators arranged in a stationary manner under the bottom transport surface, wherein the plurality of first electromagnetic actuators move a sample container carder arranged on the bottom transport surface by applying a magnetic force to the sample container carrier;
    a plurality of second electromagnetic actuators arranged in a stationary manner under the top transport surface, wherein the plurality of second electromagnetic actuators move a sample container carder arranged on the top transport surface by applying a magnetic force to the sample container carrier;
    a vertical conveying device configured to transport the sample containers contained in the sample container carriers between the bottom transport surface and the top transport surface, the vertical conveying device comprises:
        a plurality of conveying elements having conveying surfaces for placing on and carrying at least one sample container carrier;
        a circulating device to circulate the conveying elements between the bottom level and the top level in operation such that the conveying surfaces continuously remain aligned horizontally during the circulation; and
        at least one electromagnetic actuator to apply a driving force to a sample container carrier to be driven on one of the conveying surfaces; and
    a control device configured to actuate the electromagnetic actuators arranged under the bottom transport and top transport surface such that a respective sample container carrier is moved along a definable movement path on the bottom transport and top transport surface, to actuate the at least one electromagnetic actuator to apply a driving force to a sample container carrier to be driven on one of the conveying surfaces such that the sample container carrier is moved from the bottom transport surface or top transport surface in the direction of one of the conveying surfaces or from one of the conveying surfaces in the direction of the bottom transport surface or top transport surface, and to control the circulating device such that the sample container carrier is transported between the bottom transport surface and the top transport surface level.

2. The sample distribution system according to claim 1, wherein an electromagnetic actuator assigned to the conveying element is arranged below a conveying surface.

3. The sample distribution system according to claim 1, wherein the circulating device circulates the conveying elements in operation along a circulating path which is described by all the conveying elements.

4. The vertical conveying device according to claim 3, wherein the conveying elements are arranged spaced apart from one another at regular distances along the circulating path.

5. The vertical conveying device according to claim 3, wherein the circulating path comprises a first vertical portion and a second vertical portion parallel to the first vertical portion, the first vertical portion and the second vertical portion extending between the bottom level and the top level.

6. The vertical conveying device according to claim 5, wherein, in operation, the circulating device moves the conveying elements along the first vertical portion from the bottom level to the top level and moves the conveying elements along the second vertical portion from the top level to the bottom level.

7. The sample distribution system according to claim 1, wherein each conveying element comprises a detection device for a sample container carrier situated on the conveying surface of the conveying element.

8. A laboratory automation system, the laboratory automation system comprising:
    a plurality of pre-analytical, analytical and/or post-analytical stations to process sample containers and/or samples contained in sample containers; and
    a sample distribution system for distributing the sample containers between the pre-analytical, analytical and/or post-analytical stations according to claim 1.

* * * * *